United States Patent
Zhang et al.

(10) Patent No.: US 11,623,968 B2
(45) Date of Patent: Apr. 11, 2023

(54) METHOD FOR PREPARATION OF XANTHAN GUM COPOLYMER NANOMICELLES

(71) Applicant: JIANGNAN UNIVERSITY, Jiangsu (CN)

(72) Inventors: Liping Zhang, Jiangsu (CN); Caihua Ni, Jiangsu (CN); Ren Liu, Jiangsu (CN); Gang Wang, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 330 days.

(21) Appl. No.: 16/954,734

(22) PCT Filed: Nov. 26, 2019

(86) PCT No.: PCT/CN2019/120773
§ 371 (c)(1),
(2) Date: Jun. 17, 2020

(87) PCT Pub. No.: WO2021/017335
PCT Pub. Date: Feb. 4, 2021

(65) Prior Publication Data
US 2021/0032375 A1    Feb. 4, 2021

(30) Foreign Application Priority Data

Jul. 31, 2019  (CN) .......................... 201910700200.0

(51) Int. Cl.
*C08B 37/00*   (2006.01)
*A61K 9/107*   (2006.01)
(Continued)

(52) U.S. Cl.
CPC ........ *C08B 37/0033* (2013.01); *A61K 9/1075* (2013.01); *A61K 9/14* (2013.01);
(Continued)

(58) Field of Classification Search
None
See application file for complete search history.

(56) References Cited

U.S. PATENT DOCUMENTS

2009/0017120 A1   1/2009   Trimble et al.
2016/0008282 A1*  1/2016   Hong ................... C08G 63/664
                                                               514/648

FOREIGN PATENT DOCUMENTS

CN    103002885 A    3/2013
CN    103083222 A    5/2013
(Continued)

OTHER PUBLICATIONS

Google Translate. English Translation of CN 107308112 A. Accessed at https://patents.google.com/patent/CN107308112A/en?oq=CN+110302155 on Aug. 3, 2022, originally published in Chinese on Apr. 7, 2017, pp. 1-9. (Year: 2017).*

(Continued)

*Primary Examiner* — Isaac Shomer
(74) *Attorney, Agent, or Firm* — Enshan Hong; MagStone Law, LLP

(57) ABSTRACT

A method for making xanthan gum copolymer nanomicelles comprising: 1) degrading xanthan gum in aqueous solution to obtain degraded xanthan gum; 2) preparing xanthan gum bromide from the degraded xanthan gum; 3) preparing xanthan gum copolymer from the xanthan gum bromide and 4) making the gum copolymer nanomicelles from the xanthan gum copolymer. The xanthan gum copolymer nanomicelles have good morphological regularity, good biocompatibility and stable performance as an anticancer drug carriers.

8 Claims, 2 Drawing Sheets

(51) Int. Cl.
    *A61K 9/14*     (2006.01)
    *A61K 31/723*     (2006.01)
    *B82Y 5/00*     (2011.01)
    *B82Y 30/00*     (2011.01)
    *B82Y 40/00*     (2011.01)

(52) U.S. Cl.
    CPC ............ *A61K 31/723* (2013.01); *B82Y 5/00* (2013.01); *B82Y 30/00* (2013.01); *B82Y 40/00* (2013.01)

(56) References Cited

FOREIGN PATENT DOCUMENTS

| | | | | |
|---|---|---|---|---|
| CN | 105658633 | A | | 6/2016 |
| CN | 107308112 | A | * | 11/2017 ........... A61K 31/704 |
| CN | 107308112 | A | | 11/2017 |
| CN | 110302155 | A | | 10/2019 |
| JP | 104188926 | A | | 12/2014 |

OTHER PUBLICATIONS

Sheela A. Abraham, Dawn N. Waterhouse, Lawrence D. Mayer, Pieter R. Cullis, Thomas D. Madden, Marcel B. Bally. "[4] The Liposomal Formulation of Doxorubicin." Methods in Enzymology, vol. 391, 2005, pp. 71-97. (Year: 2005).*

Ying-Ling Liu, Min-Tzu Luo, and Juin-Yih Lai. "Poly(tetrafluoroethylene) Film Surface Functionalization with 2-Bromoisobutyryl Bromide as Initiator for Surface-Initiated Atom-Transfer Radical Polymerization." Macromolecular Rapid Communications, vol. 28, 2007, pp. 329-333. (Year: 2007).*

Yifen Wen and Jung Kwon Oh. "Recent Strategies to Develop Polysaccharide-Based Nanomaterials for Biomedical Applications." Macromolecular Rapid Communications, vol. 35, 2014, pp. 1819-1832. (Year: 2014).*

International Search Report dated Apr. 29, 2020 for related PCT/CN2019/120773 filed Nov. 26, 2019.

Written Opinion dated Apr. 29, 2020 for related PCT/CN2019/120773 filed Nov. 26, 2019.

* cited by examiner

METHOD FOR PREPARATION OF XANTHAN GUM COPOLYMER NANOMICELLES

RELATED APPLICATIONS

This is a U.S. national stage of international application No. PCT/CN2019/120773 filed on Nov. 26, 2019, which claims priority from China Patent Application No. 2019107002000 filed on Jul. 31, 2019, the entire content of which is incorporated herein as reference.

BACKGROUND OF THE INVENTION

1. Technical Field

The invention relates to the technical field of medical macromolecule materials, particularly, to preparation and application of xanthan gum copolymer nanomicelles.

2. Background Art

Xanthan gum is a kind of extracellular water-soluble polysaccharide secreted from *Xanthomonas campestris*. Due to its good biocompatibility and biodegradability, xanthan gum has been widely used in industry, agriculture, medicine, daily chemical industry and other fields. In the medical field, xanthan gum is mainly used as adhesive, disintegrant and agent for sustained-release and controlled-release. It is a component of capsules in microcapsule drugs and plays an important role in controlled drug release. Xanthan gum has suitable viscosity and swelling coefficient, which can prolong the gastric retention time of food and reduce blood lipid. Therefore, it has been widely used for oral drug carriers and biological scaffold gels.

Nanoparticles are targeted to specific tissues. Xanthan gum nanomicelles have long circulating time in vivo and can reduce the capture by macrophages. Xanthan gum nanomicelles not only remain the general characteristics of xanthan gum, but also have the general properties of nanomaterials such as surface and interface effects. It is of great significance in the field of controlled drug release due to its high efficiency and low toxicity.

Although xanthan gum has good chemical properties, it still has some defects as a carrier of anticancer drugs. Xanthan gum has very high molecular weight and viscosity in aqueous solution. It is difficulty to modify xanthan gum. Some hydrophobic modifications to xanthan gum have been reported. For example, xanthan gum reacted with 1-chlorohexadecane to form hydrophobically modified xanthan gum. Phthalic anhydride reacted with xanthan gum for introducing some hydrophobic phenyl groups, but the degree of modification was not easy to control and the distribution of nanoparticles size is too wide.

Therefore, it is necessary to prepare xanthan gum nanomicelles with good morphological regularity, narrow distribution of molecular weight and particle sizes. Additionally, it is also necessary to study a preparation method which is easy to control and to operate.

SUMMARY OF THE INVENTION

To overcome the above problems, the invention provides a preparation method of xanthan gum copolymer nanomicelles, which comprises the following steps:

Step 1, Pretreatment: xanthan gum in aqueous solution with a concentration of 0.5 w % is degraded, its dynamic viscosity is reduced to 110 mPa·s, then the degraded xanthan gum is obtained after drying, crushing and sieving;

Step 2, Preparation of xanthan gum bromide: the degraded xanthan gum from step 1 is dissolved in N, N-dimethylformamide, then 2-bromoisobutyl bromide solution in N, N-dimethylformamide is prepared in an ice bath under stirring, the 2 bromoisobutyl 2 bromoisobutyryl bromide solution is added to the degraded xanthan gum solution, and triethylamine is added, the reaction is carried out at the room temperature for 48 hours, the product is precipitated by ether and is filtrated, xanthan gum bromide is obtained after drying at a constant temperature of 30° C.;

Step 3, Preparation of xanthan gum copolymers: the xanthan gum bromide obtained in step 2 is dissolved in N, N-dimethylformamide, then diacetone acrylamide is added, the air in the reaction vessel is excluded by vacuum-pumping and nitrogen-charging for three times, next, tri[2-(dimethylamino) ethyl] amine and cuprous chloride are added, the reaction is carried out at 55-65° C. for 3-5 hours, the product is precipitated by ether, filtered and ished by ether for three times, finally, xanthan gum copolymers are obtained after drying at the constant temperature of 30° C.;

Step 4, Preparation of xanthan gum copolymer nanomicelles: the xanthan gum copolymers of step 3 is dissolved in polar organic solvents, and the solution is filtered by microporous filtration membranes with pore size of 0.4 um, ultra-pure water is slowly added to the xanthan gum copolymer solution until a micelle solution is formed; the micelle solution experiences dialysis against deionized water for 4 days, the dialysate is replaced by fresh deionized water every eight hours.

In the step 2 of the preparation method, the weight concentration of xanthan gum in N, N-dimethylformamide is 1.8%~2.5%, the weight concentration of 2-bromoisobutyryl bromide in the reaction system is 1.5%~2.2%, and the weight of triethylamine is 40%~60% of 2-bromoisobutyryl bromide.

In the step 3 of the preparation method, the weight of diacetone acrylamide is 1~3 times that of xanthan gum bromide; the molar ratio of tri [2-(dimethylamino) ethyl] amine to cuprous chloride is 1:1.5~2.0, preferably, the reaction temperature is 60° C. and the reaction time is 4.5 hours.

In the step 4 of the preparation method, the polar organic solvents include anhydrous ethanol, isopropanol, tetrahydrofuran, N, N-dimethylformamide, dioxane or dimethyl sulfoxide.

Another object of the present invention is to provide an application of xanthan gum copolymer nanomicelles. The nanomicelles prepared in this invention are freeze-dried to powder, an anticancer drug is dissolved in methanol to make a solution with concentration of 2 mg/ml; then, the nanomicelles powder 30 mg is added into 8 mL of the methanol solution with the anticancer drug, stirring for 5 hours; the mixed solution is transferred to a dialysis bag with the cutoff molecular weight 3500 for dialyzing 18 hours, the drug-loaded nanoparticles are obtained.

In the embodiments, the anticancer drugs include paclitaxel or 10-hydroxycamptothecin.

With the above scheme, the invention has at least the following advantages:

1. Poly(diacetone acrylamide) is grafted onto xanthan gum by living radical polymerization, the grafting degree and the particle size of nanomicelles are controllable, and the morphology of nanomicelles is well regulated.

2. Xanthan gum copolymer nanomicelles have good biocompatibility and can be used as anti-cancer drug carriers with advantages of stable performance, non-toxicity and low cost.

DESCRIPTION OF PREFERRED EMBODIMENTS

Embodiment 1

Figure 1:
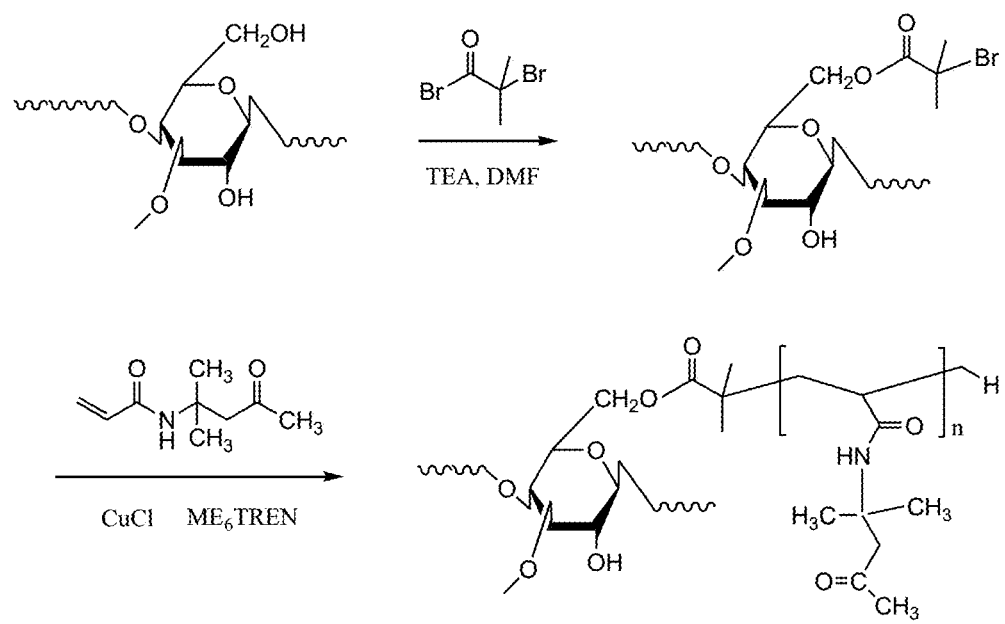
FIG. 1 Schematic diagram for the preparation of xanthan gum copolymer nanomicelles in the invention.

(1). Xanthan gum pretreatment: xanthan gum 1 g is weighed and added into 200 mL distilled water under stirring until completely dissolved, forming a solution with concentration of 0.5 w %; the solution is placed in ultrasonic environment with power of 200 W and ultrasonic frequency of 20 kHz, the ultrasonic degradation last for 2.5 hours. In the process of xanthan gum degradation, the dynamic viscosity of the xanthan gum solution is measured under different conditions by NDJ-99 rotary viscometer, the sample solution is loaded into a flat-bottomed centrifugal tube, S05 rotor is employed. The conditions for measuring the dynamic viscosity are set as 25° C. and 60 r/min. The initial dynamic viscosity of the xanthan gum solution with 0.5 w % concentration is 490 mPa·s, but the viscosity decreases to 110 mPa·s after 2.5 hours ultrasound degradation. Then the product is precipitated with ethanol, dried at 30° C., crushed and sifted with 100 mesh sieve.

(2). Preparation of xanthan gum bromide: the degraded xanthan gum 2 g is added to 250 mL three-necked flask, followed by addition of 100 mL N,N-dimethylformamide; 2.3 g of 2-bromoisobutyryl bromide is dissolved in 10 mL N,N-dimethylformamide under ice bath stirring conditions, and added to xanthan gum solution. Then, 1.2 g triethylamine (code: TEA) is added to the above solution. The reaction is carried out at the room temperature for 48 hours. The product is precipitated by adding ether, filtered and dried at constant temperature for 30° C. to obtain xanthan gum bromide (XGB).

(3). Preparation of grafted xanthan gum copolymer: The xanthan gum bromide from the above is dissolved in 50 mL of N,N-dimethylformamide, 2.0 g of diacetone acrylamide (DAA) is added, the air in the reaction vessel is excluded by vacuum-pumping and nitrogen-charging for three times, next, tri[2-(dimethylamino) ethyl] amine 0.69 g and cuprous chloride 0.594 g are added. The reaction is carried out at 60° C. for 4.5 hours, the product is precipitated by ether, filtered and washed by ether for three times, finally, xanthan gum copolymers, marked as a, are obtained after drying at the constant temperature of 30° C.;

(4). Preparation of xanthan gum copolymer nanomicelles: The grafted xanthan gum copolymer from the above is dissolved in N,N-dimethylformamide to form a solution with initial concentration of 1%. The solution is filtered by a microporous filter membrane with a pore size of 0.4 um. Ultrapure water is slowly added to the solution under stirring until a micellar solution is formed. The micellar solution is dialyzed in deionized water for 4 days, the dialysate is replaced by fresh deionized water every 8 hours in the process of dialysis. Finally, xanthan gum copolymer nanomicelles, marked as a1, is obtained.

Embodiment 2

The steps (1), (2) and (4) are the same as in embodiment 1, but in step (3), xanthan gum copolymer b is obtained by changing weight of diacetone acrylamide to 3 g for the reaction, the other process are unchanged. Finally, xanthan gum copolymer nanomicelles, marked as b1, is obtained.

Embodiment 3

The steps (1), (2) and (4) are the same as in embodiment 1, but in step (3), xanthan gum copolymer c is obtained by changing weight of diacetone acrylamide to 4 g for the reaction, the other process are unchanged. Finally, xanthan gum copolymer nanomicelles, marked as c1, is obtained.

Embodiment 4

The steps (1), (2) and (4) are the same as in embodiment 1, but in step (3), xanthan gum copolymer d is obtained by changing weight of diacetone acrylamide to 6 g for the reaction, the other process are unchanged. Finally, xanthan gum copolymer nanomicelles, marked as d1, is obtained.

Embodiment 5

Figure 2:
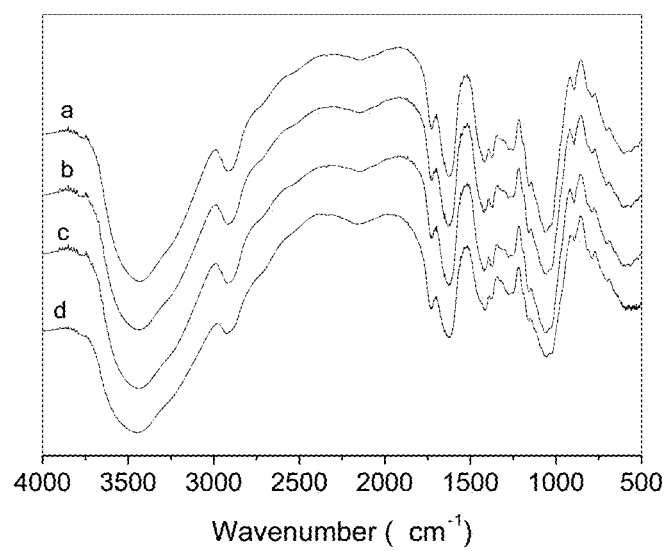
FIG. 2 Infrared spectra of xanthan gum copolymers, in which a, b, c and d correspond to xanthan gum copolymers in the embodiments 1~4, respectively.

Infrared spectra of xanthan gum copolymers: The xanthan gum copolymers a, b, c and d obtained in embodiments 1~4 are dried, a few samples and a suitable amount of KBr solid powder are mixed, grinded to fine powder under a heating lamp, pressed into thin sheets, and pressed into a Fourier transform near infrared spectrometer. Infrared spectra of the four samples are tested respectively. The instrument adopts WQF-600N Fourier Transform Infrared Spectrometer. It can be seen in FIG. 2 that the broad absorption peaks of 3300 $cm^{-1}$ and 3500 $cm^{-1}$ are obviously the overlap of the absorption peaks of hydroxyl and carboxyl groups in xanthan gum; the peak at 1660 $cm^{-1}$ is ascribed to the C=O absorption in amide bond I region of diacetone acrylamide; the peaks at 1500 $cm^{-1}$ to 1560 $cm^{-1}$ are ascribed to the absorption in amide II region; the peaks at 2900 $cm^{-1}$ and 2950 $cm^{-1}$ belong to stretching vibration of $CH_3$ and $CH_2$ respectively. It is confirmed that poly(diacetone acrylamide) was grafted onto xanthan gum.

Embodiment 6

Determination of molecular weights of xanthan gum copolymers: The xanthan gum copolymers samples a, b, c and d prepared in embodiments 1~4 are dissolved in tetrahydrofuran solution, respectively, then filtered by a filter membrane having 0.4 μm pore size, and tetrahydrofuran was used as mobile phase. The molecular weights of xanthan gum copolymers are determined by Waters 1525EF high performance liquid chromatography. The results show that the number average molecular weight increases linearly with the increase of diacetone acrylamide dosage, and the molecular weight distribution indices are less than 2. The results show that the graft copolymerization of diacetone acrylamide from xanthan gum belongs to living polymerization, and the molecular weight of the copolymers can be controlled by the dosage of diacetone acrylamide.

TABLE 1

Preparation and Molecular Weight ($\overline{Mn}$) of Xanthan Gum Copolymers

| Sample ID | Embodiment | XGB (g) (In Feed) | DA(g) | $\overline{Mn}$ | Distribution index |
|---|---|---|---|---|---|
| a | 1 | 2.0 | 2.0 | 24400 | 1.24 |
| b | 2 | 2.0 | 3.0 | 30200 | 1.19 |
| c | 3 | 2.0 | 4.0 | 37800 | 1.32 |
| d | 4 | 2.0 | 6.0 | 48200 | 1.26 |

Notes:
XGB, xanthan gum bromide; DA, diacetone acrylamide;

Embodiment 7

Measurements of Zeta potential of xanthan gum copolymer nanomicelles: The xanthan gum copolymer nanomicelles a1, b1, c1 and d1 prepared in embodiments 1~4 are used as solutions. The pH value of nanomicelles solution is adjusted to 7.4 by 0.1 M sodium hydroxide and 0.1 M hydrochloric acid. The particle size and Zeta potential of nanomicelles were measured by Zeta PALS Zeta potential and nanoparticle size analyzer. The temperature is 25° C. The results are shown in Table 2. It is observed that the size of nanomicelles increases with the increase of diacetone acrylamide dosage. This is because when the content of poly(diacetone acrylamide) in the copolymer increases, the hydrophobic component increases and it is easier to agglomerate into larger particles. At the same time, it is found that the Zeta potential of xanthan gum copolymer nanomicelles decreases with the increase of diacetone acrylamide content, because the negative charges are provided by xanthan gum which carries carboxyl negative ions, their content decreases with the increase of diacetone acrylamide content.

TABLE 2

Properties of Xanthan Gum Copolymer Nanomicelles

| Sample ID | Embodiment | Diameter (nm) | Zeta potential (mV) |
|---|---|---|---|
| a1 | 1 | 281 | −27.7 |
| b1 | 2 | 298 | −26.2 |
| c1 | 3 | 325 | −25.8 |
| d1 | 4 | 350 | −23.6 |

Embodiment 8

Figure 3:
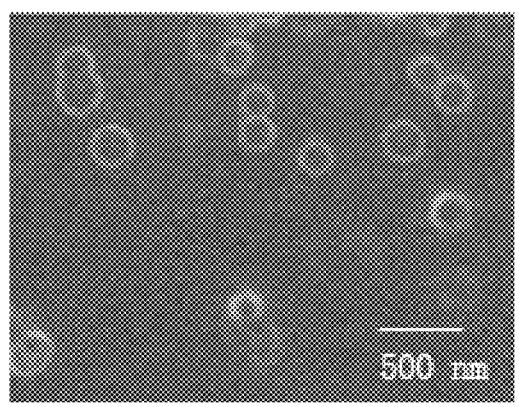
FIG. 3 Scanning electron microscopy of xanthan gum copolymer nanomicelles sample a1 obtained in embodiment 1 of the invention.

Morphological observation of xanthan gum copolymer nanomicelles: Firstly, xanthan gum copolymer nanomicelles are made into 0.1 wt % aqueous solution and dialyzed for 72 hours. Deionized water was used as external dialysate which is replaced every 3 hours to remove impurities. Then, the nanomicelle solution is dried on silicon wafer at 40° C. and sprayed with gold to obtain xanthan gum nanomicelle samples. The morphology of nanomicelles was observed by scanning electron microscopy (SEM). From FIG. 3, we can see that the morphology of nanomicelles is regular and spherical, and the distribution of nanomicelles is nearly uniform.

Embodiment 9

Preparation of xanthan gum copolymer nanomicelles: The xanthan gum copolymer nanomicelles a1, b1, c1 and d1 prepared in embodiments 1~4 are freeze-dried into powder, and the anticancer drug is dissolved in methanol to form a solution of 2 mg/mL. Then, 30 mg of nanomicelle powder is added into 8 mL of the methanol solution containing the anticancer drug. After stirring for 5 hours, the solution is transferred to a dialysis bag with cutoff molecular weight 3500. The dialysis is carried out in ultrapure water for 18 hours, the drug-loaded nanomicelles are obtained. The anticancer drug is paclitaxel or 10-hydroxycamptothecin. Table 3 shows that the drug loading rate of nanomicelles increases with the increase of diacetone acrylamide content.

TABLE 3

Drug loading rate of xanthan gum copolymer nanomicelles (%)

| Sample ID | Paclitaxel (%) | 10-hydroxycamptothecin (%) |
|---|---|---|
| a1 | 10.5 | 11.4 |
| b1 | 11.9 | 12.7 |
| c1 | 12.1 | 13.6 |
| d1 | 13.6 | 14.8 |

Embodiment 10

Biocompatibility test of Xanthan Gum Copolymer Nanomicelles

HeLa cells are diluted into $6 \times 10^4$/mL cell density by RPMI-1640 complete medium and inoculated on 96-well plate. 100 L is inoculated in each hole, and then discarded after cell adherence. The experimental group involves four nanomicelle samples a1, b1, c1 and d1. The nanomicelle sample with concentration of 1.0 mg/mL is added into 100 µL RPMI-1640 complete medium. The positive control group is RPMI-1640 complete medium containing 0.64% phenol, and the negative control group is RPMI-1640 complete medium. Four holes are arranged in parallel for each group. The cells are cultured in the incubator at 37° C. The growth morphology of the cells was observed by inverted biomicroscopy at different time.

The 96-well plate is placed in incubator for 24 hours and then removed. 10 µL MTT (5.0 mg/mL) is added to each hole and cultured at 37° C. for 4 hours, and then removed.

150 µL DMSO was added to each hole and placed in incubator for 15 minutes to dissolve the crystal violet. The absorbance A was measured by enzyme scaler at 570 nm. The cell viability (%) is calculated according to the following formula:

$$\text{Cell viability (\%)} = A_1/A_2 \times 100$$

Where $A_1$ and $A_2$ indicate the absorbance at 570 nm of the experimental group and the negative control group, respectively.

The results show that the HeLa cell viabilities are 95.8%, 93.6%, 94.3% and 94.7% respectively, after incubating at 37° C. for 28 hours with the nanomicelle samples a1, b1, c1 and d1 respectively, which proves that the nanomicelles have no cytotoxicity.

The above embodiments are only used to illustrate the technical scheme of the invention, but not to limit it. The people skilled in the field should understand that the technical scheme of the invention may be modified or replaced equally without departing from the purpose and scope of the invention, and they shall all be covered in the scope of the claims of the invention.

What is claimed is:

1. A method for making xanthan gum copolymer nanomicelles comprising:

1) degrading xanthan gum in an aqueous solution so that dynamic viscosity of the xanthan gum aqueous solution is reduced as compared with non-degraded xanthan gum, then conducting drying, crushing and sieving to obtain degraded xanthan gum;
2) dissolving the degraded xanthan gum obtained in step 1) in N, N-dimethylformamide to obtain a degraded xanthan gum solution, dissolving 2 bromoisobutyryl bromide in N, N-dimethylformamide in an ice bath under stirring to prepare 2 bromoisobutyryl bromide solution, mixing the 2 bromoisobutyl 2 bromoisobutyryl bromide solution with the degraded xanthan gum solution and then triethylamine to carry out a reaction at room temperature, then conducting precipitation with ether, filtering, and drying to obtain xanthan gum bromide;
3) dissolving the xanthan gum bromide obtained in step 2) in N, N-dimethylformamide to obtain a xanthan gum bromide solution in N, N-dimethylformamide, mixing diacetone acrylamide with the xanthan gum bromide solution in N, N-dimethylformamide in a reaction vessel, replacing air in the reaction vessel with nitrogen, then adding tri [2-(dimethylamino) ethyl] amine and cuprous chloride to the reaction vessel to carry out reaction at 55-65° C. for 3-5 hours, conducting precipitation by ether, filtering, washing, and drying to obtain xanthan gum copolymer, and
4) dissolving the xanthan gum copolymer of step 3) in a polar organic solvent, then conducting filtering with a microporous filtration membrane to obtain filtered xanthan gum copolymer solution, adding water to the filtered xanthan gum copolymer solution until a micellar solution is formed, dialyzing the micellar solution in deionized water to obtain the gum copolymer nanomicelles.

2. The method of claim 1, wherein in step 2), the degraded xanthan gum solution in N, N-dimethylformamide has a concentration of 1.8%~2.5% of degraded xanthan gum by weight.

3. The method of claim 1, wherein the amount of triethylamine is 40%-60% of the amount of 2-bromoisobutyryl bromide by weight.

4. The method of claim 1, wherein in step 3), the weight of diacetone acrylamide is 1-3 times that of xanthan gum bromide.

5. The method of claim 1, wherein in step 3), the molar ratio of tri [2-(dimethylamino) ethyl] amine to cuprous chloride is 1:1.5~2.0.

6. The method of claim 1, wherein in step 4), the polar organic solvent is selected from the group consisting of anhydrous ethanol, isopropanol, tetrahydrofuran, N, N-dimethylformamide, dioxane, dimethyl sulfoxide, and combinations thereof.

7. A method of making anti-cancer drug-loaded nanoparticles comprising:
   a) obtaining xanthan gum copolymer nanomicelles;
   b) freeze-drying the xanthan gum copolymer nanomicelles to obtain copolymer nanomicelles powder;
   c) dissolving an anticancer compound in methanol to make an anticancer drug solution;
   d) mixing the copolymer nanomicelles powder of step b) with the anticancer drug solution of step c) to obtain a mixture; and
   e) dialyzing the mixture of step d) to obtain the anticancer drug-loaded nanoparticles,
   wherein the step a) comprises:
      1) degrading xanthan gum in an aqueous solution so that dynamic viscosity of the xanthan gum aqueous solution is reduced as compared with non-degraded xanthan gum, then conducting drying, crushing and sieving to obtain degraded xanthan gum;
      2) dissolving the degraded xanthan gum obtained in step 1) in N, N-dimethylformamide to obtain a degraded xanthan gum solution, dissolving 2-bromoisobutyryl bromide in N, N-dimethylformamide in an ice bath under stirring to prepare 2-bromoisobutyryl bromide solution, mixing the 2-bromoisobutyryl bromide solution with the degraded xanthan gum solution and then triethylamine to carry out a reaction at room temperature, then conducting precipitation with ether, filtering, and drying to obtain xanthan gum bromide;
      3) dissolving the xanthan gum bromide obtained in step 2) in N, N-dimethylformamide to obtain a xanthan gum bromide solution in N, N-dimethylformamide, mixing diacetone acrylamide with the xanthan gum bromide solution in N, N-dimethylformamide in a reaction vessel, replacing air in the reaction vessel with nitrogen, then adding tri [2-(dimethylamino) ethyl] amine and cuprous chloride to the reaction vessel to carry out reaction at 55-65° C. for 3-5 hours, conducting precipitation by ether, filtering, washing, and drying to obtain xanthan gum copolymer, and
      4) dissolving the xanthan gum copolymer of step 3) in a polar organic solvent, then conducting filtering with a microporous filtration membrane to obtain filtered xanthan gum copolymer solution, adding water to the filtered xanthan gum copolymer solution until a micellar solution is formed, dialyzing the micellar solution in deionized water to obtain the gum copolymer nanomicelles.

8. The method of claim 7 wherein the anticancer drug is selected from the group consisting of paclitaxel, 10-hydroxycamptothecin, and combinations thereof.

* * * * *